US010495653B2

(12) United States Patent
Ebrahim et al.

(10) Patent No.: US 10,495,653 B2
(45) Date of Patent: *Dec. 3, 2019

(54) STABILIZATION OF LABILE ANALYTES IN REFERENCE MATERIALS

(71) Applicant: Bio-Rad Laboratories, Inc., Hercules, CA (US)

(72) Inventors: Alireza Ebrahim, Laguna Niguel, CA (US); Karl De Vore, Coto de Caza, CA (US); Christopher Spates, Laguna Hills, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/411,775

(22) Filed: Jan. 20, 2017

(65) Prior Publication Data

US 2017/0131302 A1    May 11, 2017

Related U.S. Application Data

(63) Continuation of application No. 15/331,638, filed on Oct. 21, 2016, which is a continuation of application No. 14/270,701, filed on May 6, 2014, now Pat. No. 9,506,939.

(60) Provisional application No. 61/819,758, filed on May 6, 2013.

(51) Int. Cl.
*G01N 33/96* (2006.01)
*F26B 5/06* (2006.01)

(52) U.S. Cl.
CPC ............. *G01N 33/96* (2013.01); *F26B 5/06* (2013.01); *G01N 2496/80* (2013.01)

(58) Field of Classification Search
None
See application file for complete search history.

(56) References Cited

U.S. PATENT DOCUMENTS

| | | | |
|---|---|---|---|
| 4,190,419 A | 2/1980 | Bauer | |
| 4,571,383 A | 2/1986 | Takayama et al. | |
| 4,716,119 A | 12/1987 | Rehner et al. | |
| 4,801,538 A | 1/1989 | Hanada et al. | |
| 4,931,392 A * | 6/1990 | Rehner | C12N 9/96 435/183 |
| 5,965,379 A * | 10/1999 | Tamarkin | G01N 33/533 435/12 |
| 5,998,216 A * | 12/1999 | O'Donnell | A61K 47/42 252/380 |
| 6,576,249 B1 | 6/2003 | Gendler et al. | |
| 9,506,939 B2 | 11/2016 | Ebrahim et al. | |
| 2002/0137097 A1 | 9/2002 | Nguyen et al. | |
| 2004/0152641 A1 | 8/2004 | Guthrie et al. | |
| 2005/0227225 A1 | 10/2005 | Krevolin | |
| 2005/0287624 A1 | 12/2005 | Furukawa et al. | |
| 2006/0068399 A1 | 3/2006 | McMillan et al. | |
| 2007/0117763 A1 * | 5/2007 | Guthrie | A61K 31/352 514/27 |
| 2008/0102525 A1 | 5/2008 | Rannikko et al. | |
| 2008/0153116 A1 | 6/2008 | Houen et al. | |
| 2009/0047660 A1 | 2/2009 | Lu et al. | |
| 2009/0269780 A1 | 10/2009 | Sorensen et al. | |
| 2009/0286327 A1 | 11/2009 | Cho et al. | |
| 2010/0209348 A1 | 8/2010 | Martin | |
| 2012/0270258 A1 * | 10/2012 | Adamczyk | G01N 33/721 435/29 |
| 2013/0066234 A1 | 3/2013 | Helftenbein | |
| 2013/0221281 A1 | 8/2013 | Ebrahim et al. | |
| 2013/0273021 A1 * | 10/2013 | Quinn | C12N 9/22 424/94.3 |
| 2014/0329263 A1 | 11/2014 | Ebrahim et al. | |
| 2015/0093812 A1 * | 4/2015 | Ott | A61L 27/3604 435/284.1 |
| 2016/0061694 A1 | 3/2016 | Ebrahim et al. | |

FOREIGN PATENT DOCUMENTS

| | | |
|---|---|---|
| CN | 102066899 A | 5/2011 |
| CN | 105264384 A | 1/2016 |
| EP | 2994759 A1 | 3/2016 |
| JP | 2003-520944 A | 7/2003 |
| JP | 2005-506515 A | 3/2005 |
| JP | 2016519311 A | 6/2016 |
| WO | 0106263 A1 | 1/2001 |
| WO | 02059617 A2 | 8/2002 |
| WO | 2012170549 A1 | 12/2012 |
| WO | 2013043388 A1 | 3/2013 |
| WO | 2014182666 A1 | 11/2014 |

OTHER PUBLICATIONS

English abstract for JP 2000256399;downloaded from Espacenet on Jul. 11, 2019 (Year: 2011).*
Anonymous, Bio-Rad Liquicheck Urine Chemistry Control, URL:http://www.biorad.com/webroot/web/pdf/cdg/literature/Q-1513.pdf, Jan. 1, 2012.
Anonymous, Bio-Rad Lyphocheck Quantitative Urine Control, http://www.bio-rad.com/webroot/web/pdf/cdg/literature/Q-1537.pdf, Jan. 1, 2009.
Anonymous, Creatinine in Urine-NHANES 2001-2002 Laboratory Procedure Manual, URL:https://www.cdc.gov/nchs/data/nhanes/nhanes01_02/l16bmetcreatinine.pdf, Jan. 1, 2001, 12 pages.
European Application No. 14795437.4, Extended European Search Report, dated Nov. 3, 2016, 10 pages.

(Continued)

*Primary Examiner* — Susan M Hanley

(74) *Attorney, Agent, or Firm* — Kilpatrick Townsend & Stockton LLP

(57) ABSTRACT

Provided herein are assay control materials comprising stable analytes and lyophilized unstable analytes, and methods of making and using the same.

17 Claims, 1 Drawing Sheet

(56) References Cited

OTHER PUBLICATIONS

International Application No. PCT/US2014/036920, International Preliminary Report on Patentability dated Nov. 19, 2015, 9 pages.
International Application No. PCT/US2014/036920, International Search Report and Written Opinion dated Sep. 10, 2014, 12 pages.
Final Office Action dated Aug. 7, 2018 in U.S. Appl. No. 15/331,638, filed Oct. 21, 2016. 25 pages.
Extended European Search Report dated Jul. 18, 2018 in EP Patent Application No. 18179744.0. 10 pages.
English translation of Office Action dated Nov. 26, 2018 in JP Patent Application No. 2016-513007. 2 pages.
Non-Final Office Action dated Dec. 31, 2018 in U.S. Appl. No. 15/331,638, filed Oct. 21, 2016. 10 pages.

* cited by examiner

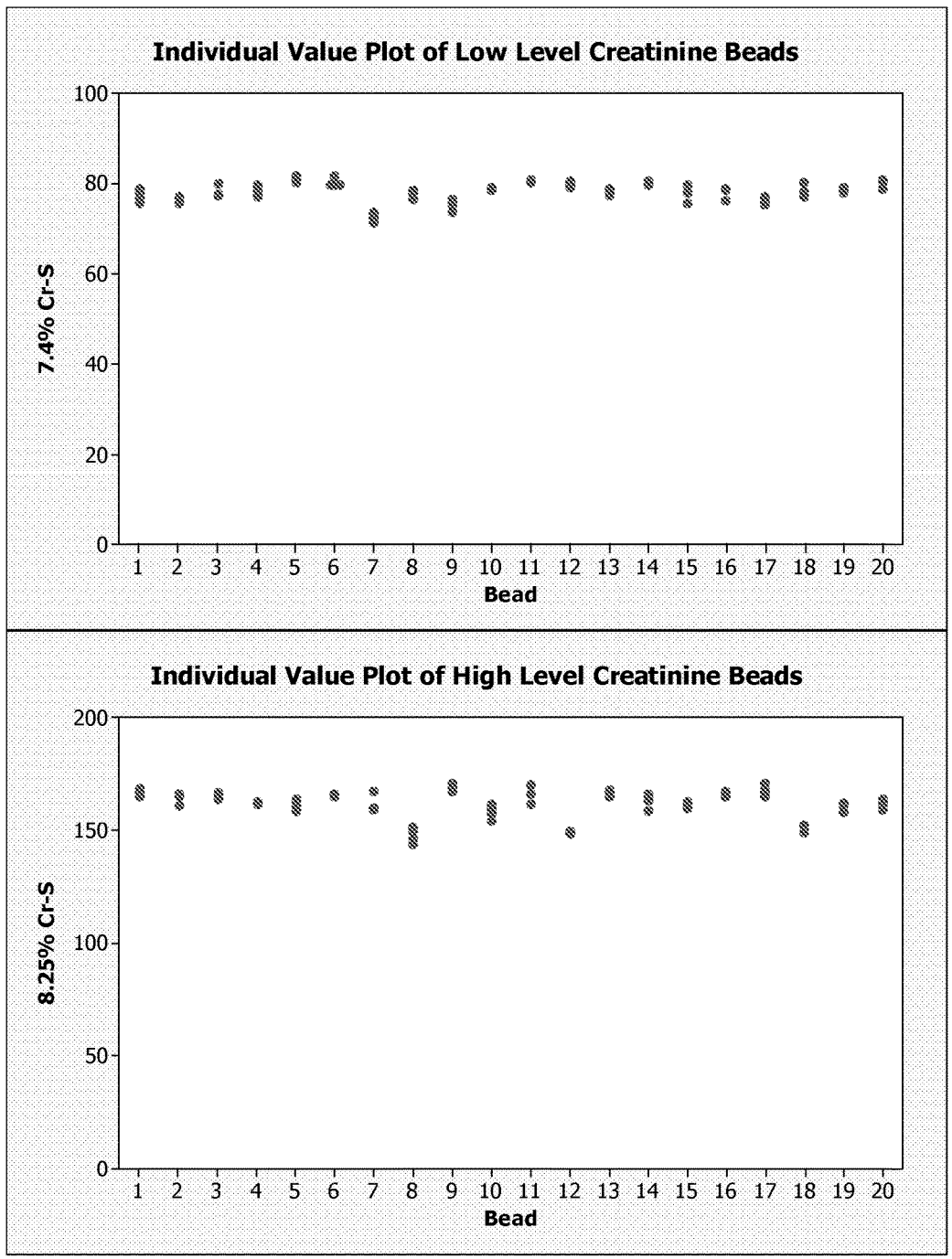

STABILIZATION OF LABILE ANALYTES IN REFERENCE MATERIALS

CROSS-REFERENCE TO RELATED APPLICATIONS

This application is a Continuation of U.S. application Ser. No. 15/331,638, filed Oct. 21, 2016, which is a Continuation of U.S. application Ser. No. 14/270,701, filed May 6, 2014, now U.S. Pat. No. 9,506,939, issued Nov. 29, 2016, which claims priority to U.S. Provisional Appl. No. 61/819,758, filed May 6, 2013, each of which is incorporated herein in its entirety.

BACKGROUND OF THE INVENTION

Commercially available quality control materials are routinely used in the clinical diagnostics laboratories to monitor the precision and accuracy of both manual and automated clinical test methods and procedures. Development of multi-analyte and multi-level quality control materials, however, is very complex due to differences in chemical and physical properties of the biomarkers/analytes in the control (molecular weight, solubility, reactivity, stability, interferences from other analytes, etc).

Multi-analyte and multi-level quality control materials typically have stability and performance limitations for at least one analyte because conditions which may improve stability of one analyte may be detrimental to stability of another. For example, Randox Liquid Chemistry Premium Plus has a performance limitation for stability of total and direct bilirubin, and the instruction pamphlet states that total and direct bilirubin values gradually decrease during the product shelf life. In addition, the instructions for MAS® ChemTRAK® Liquid Unassayed Chemistry Control (Thermo Scientific) states that bilirubin may decrease over the product shelf life and phosphorus, salicylate, and triglycerides may increase over product shelf life.

Available urine chemistry quality controls can suffer from the poor stability of creatinine. This biomarker is a clinically important analyte in commercially available urine chemistry controls because it is used to evaluate the renal function. An example of a urine chemistry quality control with poor stability for creatinine is MAS® UrichemTRAK® (Thermo Scientific). The instruction for use for this quality control states that creatinine values may decrease over the product shelf life.

BRIEF SUMMARY OF THE INVENTION

Provided herein are stable multianalyte quality control materials for monitoring the performance of various diagnostic testing methodologies in clinical laboratories. The presently described multianalyte control materials address the problem of unstable control solutions, can quickly and easily be prepared at the point of use, and can meet the quality control needs of a lab with regards to the stability of analytes. In addition to meeting the stability requirements of a quality control material, the presently described materials meet other requirements, such as responding in the same manner to the same analytical variances found in patient samples, by using human base matrices.

Provided are multianalyte control kits comprising: a first container (e.g., tube, ampoule, or vial) holding at least one unstable control analyte, wherein the at least one unstable control analyte is stabilized, e.g., by drying or lyophilization. In some embodiments, the first container holds 2, 3, 4, or 5 unstable analytes in stabilized form. In some embodiments, the first container includes more than one analyte, e.g., stable or unstable, and the analytes are all in stabilized form, e.g., dried or lyophilized. In some embodiments, the first container holds at least 2, 3, 4, 5, 6, 7, 8, 9, 10, 11, 12, 1-5, 3-10, 10-15, 10-20, or more analytes in stabilized form. In some embodiments, the at least one unstable analyte is lyophilized in the form of beads (e.g., microbeads or microspheres). In some embodiments, the bead has a diameter of 1-15 mm. In some embodiments, the at least one unstable analyte is selected from the group consisting of creatinine, bilirubin, salicylate, triglyceride, alanine aminotransferase (ALT), alkaline phosphatase, high density lipoprotein, pseudocholinesterase, folate, and homocysteine.

In some embodiments, the kit further comprises a second container holding at least one stable control analyte. In some embodiments, the at least one stable analyte is in solution. In some embodiments, the solution is a base matrix solution derived from a biological sample, e.g., processed urine, plasma, serum, saliva, synovial fluid, lymph, milk, mucus, CSF, cell lysate, or tissue culture supernatant. In some embodiments, the at least one stable control analyte is selected from the group consisting of amylase, calcium, chloride, glucose, hCG, magnesium, microalbumin, phosphorus, protein, sodium, urea nitrogen, and uric acid. In some embodiments, the at least one stable analyte is in solution at osmolality of 50-1000 mmol/kg (e.g., 100, 150, 200, 250, 300, 350, 400, 450, 500, 550, 600, 650, 700, 750, 800, 850, 900, 950, 200-800, 250-750, 400-600, etc.). In some embodiments, the at least one stable analyte is in solution at pH 4-9 (e.g., about 4-5, about 5-6, about 6-7, about 7-8, or about 8-9). In some embodiments, the base matrix solution comprises at least one component selected from: PEG, HSA, BSA, human hemoglobin, protease inhibitor, chelating agent, buffer, salt, antioxidant (or antioxidant enzyme), cryoprotectant, surfactant, and antibiotic agent (e.g., sodium azide, ciprofloxacine, chloramphenicol, gentamicin, amikacin, tobramycin, and amphotericin B).

In some embodiments, the kit further comprises a third container holding a solution for resuspending the at least one unstable analyte in the first container. In some embodiments, the third container holds a base matrix solution derived from a biological sample. In some embodiments, the solution has an osmolality of 50-1000 mmol/kg. In some embodiments the solution has a pH of 4-9. In some embodiments, the base matrix solution comprises at least one component selected from: PEG, HSA, BSA, human hemoglobin, protease inhibitor, chelating agent, buffer, salt, antioxidant (or antioxidant enzyme), cryoprotectant, surfactant, and antibiotic agent (e.g., sodium azide, ciprofloxacine, chloramphenicol, gentamicin, amikacin, tobramycin, and amphotericin B). In some embodiments, the multianalyte control kit includes at least 2, 3, 4, 5, 6, 7, 8, 9, 10, 11, 12, 1-5, 3-10, 10-15, 10-20, or more analytes.

Further provided are multilevel, multianalyte control kits comprising a first set of containers, wherein each of the first set of containers holds a different amount of at least one unstable analyte, and wherein the at least one unstable control analyte is stabilized, e.g., by drying or lyophilization. In some embodiments, the kit further comprises a second set of containers, wherein each of the second set of containers holds a different amount of at least one stable analyte. One of skill will understand that multilevel, multianalyte controls are typically designed so that all of the analytes at a given level are at a comparatively high amount, while all the analytes at another level are at a comparatively low amount, etc., depending on how many levels are contemplated. In some embodiments, the multilevel, multianalyte kit is a bilevel or trilevel kit. In some embodiments, the multilevel, multianalyte control kit includes at least 2, 3, 4, 5, 6, 7, 8, 9, 10, 11, 12, 1-5, 3-10, 10-15, 10-20, or more analytes.

In some embodiments, the multianalyte control kit used for an assay testing urine chemistry, blood serum chemistry, diabetes markers, cancer markers, immune function, or cardiovascular health.

Further provided are methods for assembling a multianalyte control kit such as those described above, comprising: (i) selecting at least one unstable analyte in the multianalyte control kit and stabilizing (e.g., drying or lyophilizing) the at least one unstable analyte in a first container and (ii) adding at least one stable analyte in the multianalyte kit to a second container. In some embodiments, the at least one unstable control analyte is lyophilized in the form of beads. In some embodiments, the at least one stable analyte is in solution. In some embodiments, the at least one unstable control analyte is selected from the group consisting of creatinine, bilirubin, salicylate, triglyceride, alanine aminotransferase (ALT), alkaline phosphatase, high density lipoprotein, pseudocholinesterase, folate, and homocysteine.

Further provided are methods for preparing a multianalyte control kit such as those described above for use in an assay, comprising: (i) resuspending at least one unstable analyte in stabilized (dried or lyophilized) form and (ii) combining the at least one unstable analyte with at least one stable analyte in solution. In some embodiments, the resuspending and combining steps are simultaneous, e.g., the at least one unstable analyte is resuspended in the solution comprising the at least one stable analyte. In some embodiments, the resuspending and combining steps are separate, e.g., the at least one unstable analyte is resuspended in a solution, and then combined with the at least one stable analyte. In some embodiments, the resuspending solution is a base matrix solution. In some embodiments, the at least one unstable analyte and at least one stable analyte are added to a base matrix solution. In some embodiments, the base matrix solution is a biological sample or derived from a biological sample, e.g., processed urine, plasma, serum, saliva, lymph, milk, mucus, CSF, cell lysate, or tissue culture supernatant. In some embodiments, the solution comprises at least one component selected from: PEG, HSA, BSA, human hemoglobin, protease inhibitor, chelating agent, buffer, salt, antioxidant (or antioxidant enzyme), cryoprotectant, surfactant, and antibiotic agent (e.g., sodium azide, ciprofloxacine, chloramphenicol, gentamicin, amikacin, tobramycin, and amphotericin B).

BRIEF DESCRIPTION OF THE DRAWINGS

FIG. 1. Bead to bead variability of creatinine beads (20 beads tested in quadruplicate).

DETAILED DESCRIPTION OF THE INVENTION

A. Introduction

Provided herein are compositions and approaches to address variable stability of analytes within mulianalyte control products. Analytes that are known to remain stable in solution are provided in a standard, ready-to-use solution, while those that are less stable in the standard solution are provided in stablized, e.g., lyophilized, form. This approach allows for more reliable results, and extended shelf life of multianalyte controls, e.g., for clinical testing facilities.

B. Definitions

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier ($4^{th}$ ed. 2007); Sambrook et al., MOLECULAR CLONING, A LABORATORY MANUAL, Cold Springs Harbor Press (Cold Springs Harbor, N.Y. 1989). The term "a" or "an" is intended to mean "one or more." The term "comprise" and variations thereof such as "comprises" and "comprising," when preceding the recitation of a step or an element, are intended to mean that the addition of further steps or elements is optional and not excluded. Any methods, devices and materials similar or equivalent to those described herein can be used in the practice of this invention. The following definitions are provided to facilitate understanding of certain terms used frequently herein and are not meant to limit the scope of the present disclosure.

The term "analyte" refers to a substance to be detected or quantitated. A "mulitanalyte" assay refers to an assay that detects or quantitates more than one analyte. Likewise, a multianalyte control will include more than one analyte in a known (control) amount. A "multilevel" control refers to a plurality of controls, each control containing the same analyte(s), where the amount of analyte(s) in each control is different. For example, a bilevel control would have two separate controls, one with a low level of the included analytes and the other with a high level of the included analytes. A trilevel control would have three separate controls, e.g., low level, mid-level, and high level.

The term "unstable analyte" can be defined quantitatively or relative to other analytes intended to be used in combination, e.g., in a multianalyte kit. The unstable analyte is one that is degraded (less detectable) after a specified time interval at the same storage condition as the stable analyte(s) by at least 0.5%, 1%, 2%, 3%, 4%, 5%, 6%, 7%, 8%, 9%, 10% or more. In some cases, an unstable analyte is one that is degraded (less detectable) after 6 months in solution at room temperature by at least 0.5%, 1%, 2%, 3%, 4%, 5%, 6%, 7%, 8%, 9%, 10% or more. In some cases, an unstable analyte is one that is degraded (less detectable) after 6 months in solution at 4° C. by at least 0.5%, 1%, 2%, 3%, 4%, 5%, 6%, 7%, 8%, 9%, 10% or more. In some cases, an unstable analyte is one that degrades faster, e.g., at rate at least 1.2-fold, 1.5-fold, 2-fold, 5-fold, or 10-fold faster, or more, than other analytes intended to be used in combination when stored in the same conditions. One of skill will understand that certain classes of molecules are likely to fall into this category, depending on storage conditions. Potentially unstable analytes include proteins (e.g., enzymes, hormones, peptides), organic molecules, and even elements that become less detectable over time when stored in a liquid.

Similarly, the term "stable analyte" can be defined quantitatively or relatively. Stability is defined in "Evaluation of Stability of In Vitro Diagnostic Method Products; Approved Guideline" (Clinical and Laboratory Standards document EP25A) as the ability of an IVD product to maintain its performance characteristics consistently over time. In some cases, a stable analyte does not detectably degrade after a significant proportion of the intended shelf life at the recommended storage condition, e.g., after 6 or 12 months in solution at room temperature. In some cases, a stable analyte does not detectably degrade after 6 or 12 months in solution at 4° C. In some embodiments, a stable analyte degrades at least 1.2-fold, 1.5-fold, 2-fold, 5-fold, or 10-fold less than at least one other analyte intended to be used in combination.

As used herein, a "base matrix solution" refers to the solution used to carry the analyte(s) for detection. A base matrix solution is chemically similar in composition to clinical samples to be tested (e.g., urine, blood, lymph, etc.), includes at least some of the same components, and is in a similar pH range. Typically, components of the clinical sample that would interfere with detection of analytes, e.g., high endogenous levels of the analyte, other analytes to be tested, fibrin, or other protein or lipid components, are removed from a base matrix solution.

The terms "label," "detectable moiety," and like terms refer to a composition detectable by spectroscopic, photochemical, biochemical, immunochemical, chemical, or other physical means. For example, useful labels include fluorescent dyes, luminescent agents, radioisotopes (e.g., $^{32}P$, $^{3}H$), electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target analyte. Any method known in the art for conjugating an antibody to the label may be employed, e.g., using methods described in Hermanson, *Bioconjugate Techniques* 1996, Academic Press, Inc., San Diego. The term "tag" can be used synonymously with the term "label," but generally refers to an affinity-based moiety, e.g., a "His tag" for purification, or a "strepavidin tag" that interacts with biotin.

A "labeled" molecule (e.g., nucleic acid, protein, or antibody) is one that is bound, either covalently, through a linker or a chemical bond, or noncovalently, through ionic, van der Waals, electrostatic, or hydrogen bonds to a label such that the presence of the molecule may be detected by detecting the presence of the label bound to the molecule.

A "control" sample or value refers to a sample that serves as a reference, usually a known reference, for comparison to a test sample. For example, a test sample can be taken from a test condition, e.g., in the presence of a test compound or in stabilized conditions, and compared to samples from known conditions, e.g., in the absence of the test compound or stabilized condition (negative control), or in the presence of a known compound or condition (positive control). A control can also represent an average value gathered from a number of tests or results. One of skill in the art will recognize that controls can be designed for assessment of any number of parameters. For example, a control can be devised to compare signal strength in given conditions, e.g., in the presence of a stabilized (e.g., lyophilized) analyte, in the absence of a stabilized analyte (negative control), or in the presence of a known stable analyte (positive controls). One of skill in the art will understand which controls are valuable in a given situation and be able to analyze data based on comparisons to control values. Controls are also valuable for determining the significance of data. For example, if values for a given parameter are variable in controls, variation in test samples will not be considered as significant.

C. Formation of Stablized Compositions

Unstable analytes can be stored in a stabilized composition such as a dry powder. The drying of a solution comprising at least one unstable analyte can be accomplished using any appropriate method, such as those described herein, lyophilization, freeze drying, or fluidized bed drying. Lyophilization typically involves inserting the solution into a vacuum chamber, or otherwise applying a vacuum to the solution (see, e.g., U.S. Pat. Nos. 7,588,942, 7,354,597, and 7,073,349). In some embodiments, heat or a drying gas is applied. Freeze drying typically involves spraying a solution through an atomizing nozzle into a cold gas phase such as liquid nitrogen (see, e.g., U.S. Pat. No. 7,007,406, Leuenberger (2002) *J. Nano. Res.* 4:111). Fluidized bed drying is described, e.g., in U.S. Pat. No. 4,624,058, Sellers et al. *J. Pharm. Sci.* 90:785, and Frake et al. (1997) *Int J. Pharm.* 151:75. Once a stabilized dry composition is obtained, it can be stored in a sealed container to maintain stability and avoid moisture or contamination.

In some embodiments, the unstable analyte(s) are added in solution to microbeads or microspheres that are designed to hold a predetermined volume of liquid. The solution of microspheres is then subjected to drying. More than one analyte can be in the solution, so that each microsphere holds more than one analyte. In some embodiments, each analyte is added at a known concentration, so that each microsphere holds a known amount of analyte. In some embodiments, stabilized compositions are formed with multiple analyte concentrations to obtain a multi-level kit, e.g., with multiple tubes, each representing a different amount of analyte(s).

D. Solutions and Components

Provided herein are solutions for analytes, or for resuspending stabilized (e.g., dryed or lyophilized) analytes. Such solutions are typically pH controlled, e.g., with a buffer such as PBS, Tris, or HEPES, so that the pH does not have an overly negative effect on the analytes in solution. Such solutions also can have stabilizing agents such as PEG or HSA. Solutions can have additives such as protease inhibitors, chelating agents, buffers, salts, antioxidants (or antioxidant enzymes), cryoprotectants, surfactants, and antibiotic agents (e.g., sodium azide, ciprofloxacine, chloramphenicol, gentamicin, amikacin, tobramycin, or amphotericin B).

The solution for analytes can be based on the composition and characteristics of the samples to be tested, e.g., a biological sample such as saliva, serum, plasma, lymph, urine, milk, mucus, CSF, cell lysate, tissue culture supernatant, etc. For example, a solution for a multianalyte control for urinalysis would be based on the composition of urine to minimize confounding differences, such as pH or salt concentrations. In some embodiments, the solution is assembled from purified components, either synthetic or biologically sourced, to mimic the biological sample (e.g., 5% HAS in 0.9% PBS or 50 mM Tris buffer with 150 mg/dL purified bovine cholesterol). In some embodiments, the solution is derived from the biological sample and processed to remove components that will interfere with detection of the analytes, e.g., analytes to be detected (e.g., in high endogenous amounts), fibrin, extraneous proteins, lipids, contaminants, or other components. Processing can include charcoal stripping to remove endogenous steroid hormones, heat treatment to reduce protease activity, or Celite treatment to reduce lipids.

E. Types of Assays and Analytes

Provided herein are compositions, kits, and methods for designing multianalyte controls with increased stability. The multianalyte control can be used with any standard bioassay or assay format. The multianalyte control can be used to compare to and quantitate components of biological samples (e.g., saliva, serum, plasma, lymph, urine, milk, mucus, CSF, cell lysate, tissue culture supernatant) or other sample types, and monitor assay performance.

The presently described multianalyte controls can be used with any multianalyte assays. Such assays have been designed for diagnosing or characterizing a number of conditions, e.g., urinalysis for kidney or liver function, anti-nuclear antibodies (ANA test), cancer (e.g., bladder, prostate, ovarian cancer), dyslipidemia, Alzheimer's disease, atherosclerosis, diabetes, cardiac function, immune function, etc.

In some embodiments, the multianalyte control is for a multianalyte urine test. In some embodiments, stable control analytes for a multianalyte urine test include any one or more (1, 2, 3, 4, 5, 6, 7, 8, 9, 10, 11, 12, or all 13) of amylase, calcium, chloride, cortisol, glucose, hCG, magnesium, microalbumin, phosphorus, potassium, sodium, urea nitrogen, and uric acid in any combination. In some embodiments, stable control analytes for a multianalyte urine test further include any one or more (1, 2, 3, 4, or all 5) of ketones, leukocyte esterase, nitrite, protein, and urobilinogen. In some embodiments, stable control analytes for a multianalyte urine test include any one or more (1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or all 37) of 3-Methoxytyramine, 5-Aminolevulinic Acid, 5-HIAA, 17-Hydroxycorticosteroids, 17-K etogenic Steroid, 17-Ketosteroid, Aldosterone, AMP (Cyclic), Arsenic, Calcium, Chloride, Coproporphyrin, Cortisol, Dopamine, Epinephrine, Glucose, EWA, Hydroxyproline, Iron, Lead, Magnesium, Mercury, Metanephrine, Microalbumin, Norepinephrine, Normetanephrine, Phosphorus, Porphyrins, Potassium, Protein, Sodium, Urea, Urea Nitrogen, Uric Acid, Uroporphyrins, VMA, and Zinc, in any combination.

In some embodiments, unstable analytes for a multianalyte urine test include creatinine. Creatinine is included in the Uric Acid, BUN, Amylase, Calcium, Magnesium, and Creatinine tests for detection on the Beckman Coulter DxC, and considered unstable relative to the other analytes in the tests. In some embodiments, unstable analytes for a multianalyte urine test include bilirubin. In some embodiments, unstable analytes for a multianalyte urine test include creatinine and bilirubin. In some embodiments, unstable analytes for a multianalyte urine test include any one or more (1, 2, 3, 4, 5, 6, 7, 8, 9, 10, 11, 12, 13, 14, 15, 16, or all 17) of 11-β-Hydroxy-Androsterone, 11-β-Hydroxy-Etiocholanolone, 11-Ketoandrosterone, 11-Ketoetiocholanolone, Androsterone, Barbiturate, Bilimbin, Copper, Coproporphyrin, Creatine, Creatinine, Cystine, Dehydroepiandrosterone, Estriol, Etiocholanolone, Hydroxyproline, Pregnanetriol, in any combination.

Multianalyte controls are often packaged or used as multilevel controls, that is, where there are a plurality of tubes containing the same analyte(s) at different levels. A multianalyte control as described herein can include a container holding at least one unstable control analyte in stablized form (unstable control level 1) and a container holding at least one stable analyte in solution (stable control level 1). A multilevel control would include additional containers, e.g., unstable control level 2, and in some embodiments, unstable control level 3, and in some embodiments, unstable control level 4, etc. The multilevel control can also include additional containers with, e.g., stable control level 2, stable control level 3, and in some embodiments, stable control level 4.

In some embodiments, the levels of the multilevel controls are prepared to cover a range, e.g., a range of normal levels for the included analytes. For example, a normal range of sodium concentrations in a 24-hour urine collection test is 40-220 mmol/day for an adult. Assuming an average urine output of 1 liter per day, an exemplary set of multianalyte controls can be prepared so that sodium will be representative in the assay of 40 and 200 mmol, optionally with intermediate levels (e.g., 120 mmol). A normal range of serum creatinine is 53-113 micromolar for an adult. An exemplary set of multianalyte controls can be prepared so that creatinine will be representative in the assay of 53 and 113 micromolar, optionally with intermediate levels. In some embodiments, the multilevel control includes containers representing 2 or 3 levels that cover normal ranges of the included analytes, e.g., a low level multianalyte control representing the low concentration of the included analyte ranges, and a high level multianalyte control representing the high concentration of the included analyte ranges. In some embodiments, the multilevel controls are prepared to include normal and abnormal levels of the included analytes. For example, higher than normal urine cortisol can be indicative of Cushing's Syndrome; normal cortisol levels for a 24 hour urine sample are usually <50 micrograms/day. Multilevel controls in this case can be prepared to represent, e.g., 20 micrograms, 50 micrograms, 100 micrograms, and 200 micrograms. One of skill can determine normal or abnormal levels of a given analyte using information available in the field, e.g., MedlinePlus from the NIH, the FDA, or the Mayo Clinic website.

F. Examples

1. Example 1: Preparation of Lyophilized Analyte Spheres

To manufacture a composition of lyophilized unstable analyte, small-diameter beads (3-9 mm), each containing a precise and accurate amount of a concentrated liquid (25-250 uL) containing one or multiple unstable analytes were dispensed and lyophilized as spheres. To help prepare consistent, stable, and durable spheres, excipients were used in the formulation of the spheres. The spheres can be produced commercially and in large scales by BioLyph, LLC (Hopkins, Minn.).

Two solutions containing 8390 mg/dL or 8665 mg/dL of creatinine in deionized water were used to prepare two different creatinine beads with different concentrations (low and high). These solutions were combined with additives, and then dispensed and lyophilized to produce the beads. The concentration of creatinine in the solution intended for production of the creatinine spheres was significantly higher than the concentration of creatinine control levels needed in order to account for the dilution factors due to addition of spheres to the reconstitution control fluid.

Table 1 and FIG. 1 show the characteristics and bead-to-bead variability of creatinine beads.

TABLE 1

Creatinine bead characteristics

| Bead | Bead Size Diameter | Dispense Volume | Mass of Bead | Mass of Analyte in Bead | Standard Deviation (+/−) | Coefficient of Variation (%) |
|---|---|---|---|---|---|---|
| Creatinine (low level) | 5 mm | 50 μL | 7.27 mg | 8.39 mg | 0.108 mg | 2.77 |

TABLE 1-continued

Creatinine bead characteristics

| Bead | Bead Size Diameter | Dispense Volume | Mass of Bead | Mass of Analyte in Bead | Standard Deviation (+/−) | Coefficient of Variation (%) |
|---|---|---|---|---|---|---|
| Creatinine (high level) | 6 mm | 100 μL | 15.3 mg | 8.65 mg | 0.319 mg | 3.69 |

2. Example 2: Preparation of Quality Control with Stable Analytes

Formulation of the Urine Chemistry Control begins by processing the normal human urine base. An enzymatic heat treatment is conducted to degrade endogenous labile creatinine. The urine is incubated with 100 U/dL Creatininase and 50 U/dL Creatinase at 25° C. for 1 hour. The next step is a 7-day, 41° C. incubation. Following treatment, the processed urine is diafiltered to remove the degradative enzymes. Finally, the collected urine is diluted with an equal volume of deionized water before testing creatinine background concentration.

TABLE 2

Endogenous creatinine concentration in urine base before and after processing

|  | Creatinine concentration |
|---|---|
| Unprocessed urine | 45.03 mg/dL |
| Creatinine degraded urine | 12.55 mg/dL |

Following the initial processing, stable analytes and other matrix constituents are added to the desired concentrations. The resulting control will have the analytes in a traditional Urine Chemistry Control except for creatinine, which can be added via lyophilized bead at the point of use. Urine chemistry controls can include any one or more of amylase, calcium, chloride, cortisol, glucose, hCG, magnesium, microalbumin, phosphorus, potassium, protein, sodium, urea, urea nitrogen, and uric acid.

3. Example 3: Preparation of the Quality Control at the Point of Use

The quality control was prepared by rehydrating the appropriate number of analyte beads (each with a defined and assayed concentration) in the appropriate volume of the quality control with stable analytes to achieve the desired concentration for each level of control. Multiple levels of control with different concentration of analyte were prepared to achieve analyte concentrations at below, near, or above the clinical decision points of the assays. Analyte concentrations were then determined to ensure multi-level and clinical utility of the composition. The resulting compositions were then capped and stored at 2-8° C.

In this example, a tri-level multi-analyte Urine Chemistry Control was formulated. Tri-level creatinine utility was achieved by adding one low-level creatinine bead to 5 mL of Level 1 control, one high-level creatinine bead to 5 mL of Level 2 control, and one of each level creatinine bead (2 beads total) to 5 mL of Level 3 control.

Table 3 shows the recovery data for analytes in a tri-level multi-analyte Urine Chemistry Control prepared at the point of use by reconstituting the lyophilized creatinine analyte sphere in a liquid urine chemistry composition containing stable analytes.

TABLE 3

Concentrations of analytes in the urine chemistry control

| Analyte | Unit | Level 1 | Level 2 | Level 3 |
|---|---|---|---|---|
| Amylase | U/L | 80 | 211 | 289 |
| Calcium | mg/dL | 7.9 | 11.6 | 20.8 |
| Chloride | mmol/L | 86 | 209 | 255 |
| Glucose | mg/dL | 32 | 336 | 393 |
| hCG | Qualitative | − | + | + |
| Magnesium | mg/dL | 4.6 | 11.2 | 20.5 |
| Microalbumin | mg/L | 34 | 127 | 184 |
| Phosphorus | mg/dL | 26.7 | 49.3 | 76.7 |
| Protein | mg/dL | 25 | 72 | 121 |
| Sodium | mmol/L | 83.8 | 178.0 | 216.7 |
| Urea Nitrogen | mg/dL | 474.1 | 745.9 | 844.5 |
| Uric Acid | mg/dL | 17.0 | 22.0 | 27.0 |
| Creatinine | mg/dL | 106.01 | 198.39 | 290.16 |

Stabilities of the analytes were evaluated by using an accelerated stability model to predict shelf life. Vials of the liquid urine chemistry control containing stable analytes and vials of creatinine beads were stored at elevated temperatures (35, 40, and 45° C.) for pre-determined periods of time to observe analyte decomposition/degradation more rapidly than the recommended storage temperature (2-8° C.). The samples were then assayed for analyte concentration at the end of various incubation periods. The results show that the analytes would be stable for at least 4 years when stored at 2-8° C. Table 4 shows the real time stability data for creatinine for the first 18 months of the study. Statistically significant results are indicated by italics.

TABLE 4

Real time stability of creatinine at 2-8° C.

| | Traditional Urine Chemistry Control | | Urine Chemistry Control of this Invention | | |
|---|---|---|---|---|---|
| Time (month) | Level 1 | Level 2 | Level 1 | Level 2 | Level 3 |
| 1 | 0.27% | *−1.19%* | 0.73% | 0.47% | 1.71% |
| 6 | −0.93% | *−3.70%* | 0.04% | −1.17% | 0.69% |
| 12 | *−4.10%* | *−8.08%* | *−1.37%* | 0.87% | 0.37% |
| 18 | *−8.79%* | *−11.69%* | −1.80% | −0.81% | −0.55% |

Open vial stability of the controls was also evaluated by simulating actual laboratory use conditions. This was done by storing the vials of controls prepared by adding creatinine beads at 2-8° C. and removing them from the refrigerator every working day for 36 days, allowing the vials to equilibrate at room temperature for 15 minutes, opening the vials and exposing their contents to the laboratory environment, and closing the vials and returning them to the recommended storage temperature of 2-8° C. Samples of the vials were assayed during this open vial stability study for analyte concentration. The results of this study indicate that all quantitative analytes from Table 3 will be stable for at least 36 days when prepared as described above and stored at 2-8° C.

It is understood that the examples and embodiments described herein are for illustrative purposes only and that various modifications or changes in light thereof will be suggested to persons skilled in the art and are to be included within the spirit and purview of this application and scope of the appended claims. All patents, patent applications, internet sources, and other published reference materials cited in this specification are incorporated herein by reference in their entireties. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A method of preparing a control from an analyte control kit, the method comprising,
suspending in a solution at least one unstable control analyte that is lyophilized in the form of beads or microspheres that contain a pre-determined amount of the at least one unstable control analyte to form a suspended unstable analyte, wherein the solution is a base matrix solution from a biological sample from which the unstable control analyte has been removed, wherein the base matrix comprises an antibiotic agent, wherein the base matrix comprises polyethylene glycol or human hemoglobin, and wherein the base matrix is a biological sample selected from processed urine, lymph, urine from which bilirubin or creatinine or both bilirubin and creatinine have been removed from the urine, milk, mucus, cell lysate, or tissue culture, wherein the processed urine is generated by a method comprising contacting urine with creatininase to remove creatinine from the urine.

2. The method of claim 1, wherein the base matrix comprises at least one stable control analyte.

3. The method of claim 2, wherein the at least one stable control analyte is selected from the group consisting of amylase, calcium, chloride, cortisol, glucose, hCG, magnesium, microalbumin, phosphorus, potassium, sodium, urea nitrogen, and uric acid.

4. The method of claim 3, wherein the base matrix further comprises one or more of ketones, leukocyte esterase, nitrite, protein, and urobilinogen.

5. The method of claim 1, wherein the at least one unstable control analyte is suspended in the solution to form two separate suspended unstable analyte solutions, wherein the two separate unstable analyte solutions have different concentrations of the unstable analyte.

6. The method of claim 1, further comprising: combining a stable control analyte with the suspended unstable analyte.

7. The method of claim 1, wherein the at least one unstable control analyte is selected from the group consisting of creatinine, bilirubin, salicylate, triglyceride, alanine aminotransferase (ALT), alkaline phosphatase, high density lipoprotein, pseudocholinesterase, folate, and homocysteine.

8. A method of preparing a control from an analyte control kit, the method comprising,
suspending in a solution at least one unstable control analyte that is lyophilized in the form of beads or microspheres that contain a pre-determined amount of the at least one unstable control analyte to form a suspended unstable analyte, wherein the at least one unstable control analyte is bilirubin or creatinine or both bilirubin and creatinine, wherein the solution is a base matrix solution from a biological sample from which the unstable control analyte has been removed, wherein the base matrix comprises an antibiotic agent, and wherein the base matrix is urine.

9. The method of claim 8, wherein the base matrix comprises at least one stable control analyte.

10. The method of claim 8, wherein the at least one unstable control analyte is suspended in the solution to form two separate suspended unstable analyte solutions, wherein the two separate unstable analyte solutions have different concentrations of the unstable analyte.

11. The method of claim 8, wherein the base matrix comprises polyethylene glycol, human serum albumin, bovine serum albumin, or human hemoglobin.

12. A method of preparing a control from an analyte control kit, the method comprising,
suspending in a solution at least one unstable control analyte that is lyophilized in the form of beads or microspheres that contain a pre-determined amount of the at least one unstable control analyte to form a suspended unstable analyte, wherein the solution is a base matrix solution from a biological sample from which the unstable control analyte has been removed, wherein the base matrix comprises an antibiotic agent, and wherein the base matrix is processed urine that was generated in a method comprising contacting urine with creatininase to remove creatinine from the urine.

13. The method of claim 12, wherein the base matrix comprises at least one stable control analyte.

14. The method of claim 12, wherein the at least one unstable control analyte is suspended in the solution to form two separate suspended unstable analyte solutions, wherein the two separate unstable analyte solutions have different concentrations of the unstable analyte.

15. The method of claim 12, wherein the base matrix comprises polyethylene glycol, human serum albumin, bovine serum albumin, or human hemoglobin.

16. The method of claim 12, wherein the at least one unstable control analyte is selected from the group consisting of creatinine, bilirubin, salicylate, triglyceride, alanine aminotransferase (ALT), alkaline phosphatase, high density lipoprotein, pseudocholinesterase, folate, and homocysteine.

17. The method of claim 12, wherein the at least one unstable control analyte is bilirubin or creatinine or both bilirubin and creatinine.

* * * * *